United States Patent [19]

Rao et al.

[11] 4,113,789

[45] Sep. 12, 1978

[54] HYDROISOMERIZATION OF NORMAL PARAFFIN WITH A CATALYST OF NOBLE METAL, ALUMINA SUPPORT AND CHLORINE

[75] Inventors: Babu Y. Rao, Fishkill; John T. Nolan, Jr.; John H. Estes, both of Wappingers Falls, all of N.Y.

[73] Assignee: Texaco Inc., New York, N.Y.

[21] Appl. No.: 774,099

[22] Filed: Mar. 3, 1977

[51] Int. Cl.$^2$ .............................................. C07C 5/30
[52] U.S. Cl. .............................. 260/683.68; 252/441; 252/442
[58] Field of Search ........... 260/683.68, 683.7, 683.75; 252/441, 442, 466 B, 683.7, 683.75

[56] References Cited

U.S. PATENT DOCUMENTS

| | | | |
|---|---|---|---|
| 3,087,977 | 4/1963 | Griffin, Jr. et al. | 260/683.7 |
| 3,112,351 | 11/1963 | Hoekstra | 260/683.75 |
| 3,215,753 | 11/1965 | Bloch et al. | 260/683.68 |
| 3,285,990 | 11/1966 | Kelly et al. | 260/683.75 |
| 3,892,683 | 7/1975 | Germanas et al. | 260/683.68 |
| 3,956,413 | 5/1976 | Hayes | 260/683.75 |
| 3,963,643 | 6/1976 | Germanas et al. | 260/683.68 |

*Primary Examiner*—George Crasanakis
*Attorney, Agent, or Firm*—Thomas H. Whaley; Carl G. Ries; George J. Darsa

[57] ABSTRACT

A process for the hydroisomerization of paraffinic hydrocarbons employing a catalyst composed of a noble metal, alumina and chlorine. The catalyst is prepared by treating a composite of noble metal and alumina with an aluminum compound such as an inorganic or organic salt of aluminum, preferably aluminum nitrate, calcining the treated composite and thereafter contacting the treated composite with a conventional chloride activating agent. By treating and calcining the composite with an aluminum salt, the amount of noble metal retained on the catalyst's surface during chloride activation is maximized enabling high conversions of normal paraffins to isoparaffins to be realized.

9 Claims, No Drawings

HYDROISOMERIZATION OF NORMAL PARAFFIN WITH A CATALYST OF NOBLE METAL, ALUMINA SUPPORT AND CHLORINE

BACKGROUND OF THE INVENTION

This invention relates to a hydrocarbon conversion process and more particularly to a process and catalyst for the isomerization of isomerizable hydrocarbons. Pursuant to this invention, a commercially useful process for the hydroisomerization of $C_4$ to $C_6$ paraffins is provided together with an improved catalyst and method of making the same.

It is known that normal paraffins having four to six carbon atoms may be isomerized to their branched chain isomers by employing chlorided metal-alumina catalysts. Isomerization catalysts of this type are typically prepared by activating a metal-alumina composite with a chloride activating agent or combination of agents as described in U.S. Pat. Nos. 3,551,516, 3,555,107 and 3,567,796, all assigned to the assignee hereof. Accordingly, isomerization catalysts can be prepared by chloriding composites of metal and alumina where the metal can be, for example, platinum, palladium, rhodium or ruthenium. The composite is contacted with, for example, a chloroalkane or an acid chloride or other chloriding system known to the art under conditions enabling the activating agent to react with the metal-alumina composite and resulting in the preparation of catalysts having a chlorine content of about 3.0 to 15.0 weight percent. The chlorided catalyst can thereafter be stabilized pursuant to the description and procedure set forth in U.S. Pat. Nos. 3,440,300 and 3,440,301.

While the procedures heretofore employed enabled the preparation of active catalysts and the isomerization of normal paraffins in the presence thereof, problems not heretofore apparent were encountered in scaling the process to commercial size operations. More specifically, in the course of preparing the catalyst by chloriding substantial amounts of metal-alumina composite, more than the stoichiometric amount of activating agent is needed so as to chloride the composite to a level of 3.0 to 15.0, typically 4.0 to 8.0, weight percent. While the use of excess activating agent produced no apparent deleterious affects when relatively small or laboratory amounts of catalyst were prepared, such is not the case when substantial amounts of catalyst are needed for commercial size operations. It has been found that the use of more than stoichiometric amounts of activating agent in commercial size operations can effect loss of metal from the composite leading to a catalyst having lower catalytic activity and an isomerization process providing less converted normal paraffins to isoparaffins. Inasmuch as the metal of choice of the isomerization catalyst is generally platinum, substantial loss of platinum from the catalyst produces severe economic penalties in terms of the cost of the catalyst and the isomerization process employing the same.

Further, the loss of metal from the catalyst can result in catalyst beds having uneven distributions of metal. For example, where an in-situ activation procedure is employed as when a bed of metal-alumina composite is contacted with a flowing stream of chloride activator, the portion of the catalyst first contacted by the stream can undergo metal depletion. As a consequence the metal content of this portion of the bed can be substantially less than that of the bed later contacted by the stream. While reduction in the amount of chloride activator employed can reduce the metal losses from the initial portion of the bed, the latter portion may undergo a somewhat lesser degree of activation in that less chloriding agent is available when contacting occurs. Further, since some channeling in the bed may occur in the course of activation, reduced amounts of activator increase the opportunity for portions of the bed not to be contacted with activating agent thereby resulting in either inactivated or poorly activated catalyst portions.

Moreover, metal-alumina composites represent materials commercially available from various sources. While the chemical compositions of the commercial or otherwise prepared composites are generally uniform or similar, the properties with respect to the composites' ability to retain metal during activation may nevertheless vary. For example, in one instance substantial amounts of metal may be depleted from the composite when contacted with the activating agent whereas another commercial lot may be more resistant to depletion of the metal. Accordingly, the known procedures for providing an activating catalyst are also dependent upon the metal-alumina composite which in turn may necessitate numerous and costly alterations in the activation procedure. A uniform method capable of preparing isomerization catalysts from composites varying in properties has not heretofore been available.

It is therefore an object of this invention to provide a process for the hydroisomerization of paraffinic hydrocarbons employing an improved catalyst composed of a noble metal, alumina and chlorine.

Another object of this invention is to provide a method for the preparation of an isomerization catalyst of high activity where the amount of metal retained on the catalyst's surface during activation is maximized.

Yet another object of this invention is to provide a method for the in situ activation of an isomerization catalyst where the loss of metal from the composite upon activation is deterred.

Other objects and advantages of this invention will become apparent from the following detailed description of the invention.

SUMMARY OF THE INVENTION

Broadly this invention contemplates a process for the hydroisomerization of paraffinic hydrocarbons employing a catalyst composed of a noble metal, alumina and chlorine, said catalyst prepared by treating a composite of a noble metal and alumina with an inorganic or organic salt of aluminum, preferably aluminum nitrate, calcining the treated composite and thereafter contacting the composite with a conventional chloride activating agent. The catalyst provided herein and employed in the hydroisomerization process comprises an alumina support, typically eta or gamma alumina, about 0.01 to about 2.0 weight percent of a noble metal on the support, about 0.1 to 2.0, preferably 0.2 to 1.0, weight percent of stabilizing alumina overlaying the metal-alumina support and about 3.0 to 15.0 weight percent chlorine. It has been found that the presence of the stabilizing alumina on the metal-alumina composite enables the loss of platinum during the activation to be substantially reduced or entirely eliminated.

Pursuant to our invention, the noble metal on alumina composite is initially treated with an organic or inorganic aluminum salt, such as the nitrate, sulfate, chloride, bromide, iodide, chlorate, bromate, acetate, lactate or alcoholate, preferably aluminum nitrate. The aluminum compound is suitably placed in a solution of water or alcohol or mixtures thereof and the metal-alumina composite is treated with the solution such that the composite is wetted and absorbs the aluminum compound. Thereafter, the composite is calcined in the presence of air at a temperature of from about 800 to about 1200° F. so as to convert the aluminum compound to a deposit of alumina. Any aluminum salt can be employed which is decomposable to alumina upon being calcined in air at about 800° to 1200° F. The alumina deposit is believed to be somewhat amorphous and resembles gamma alumina. The amount of alumina introduced to the composite is generally about 0.1 to about 2.0, preferably 0.2 to 1.0, weight percent of the finished catalyst. The calcination should be conducted for a time sufficient to enable the treated composite to possess a moisture content of not more than about 2 weight percent.

Thereafter, the noble metal, alumina support and stabilizing alumina composite is converted to an isomerization catalyst by contacting with a conventional chloride activating agent, as for example, carbon tetrachloride or an organic chloride having at least 2 carbon atoms together with chlorine or oxygen, thereby providing the activated catalytic material with from 3.0 to 15.0, preferably 4.0 to 8.0, weight percent chlorine. The activator system can be any of those described in the art, as for example, those described in U.S. Pat. Nos. 3,551,516, 3,555,107, 3,567,796, 3,646,152 and 3,689,434 which are hereby incorporated by reference. A preferred activation is undertaken in the presence of carbon tetrachloride in a dry gas, such as air, nitrogen or helium. The resulting chlorided metal-alumina catalyst may subsequently be stabilized by heating the catalyst to a temperature of from 600° to 1200° F. in a gaseous stream such as hydrogen, nitrogen, helium, oxygen or argon and thereafter contacting the catalyst with hydrogen chloride gas or chlorinated hydrocarbons, such as carbon tetrachloride, at a temperature of from about 150° to 700° F. as described in U.S. Pat. Nos. 3,440,300 and 3,440,301.

While the instant invention provides a means whereby noble metal retention is maximized, additional improvements in metal retention can be achieved by controlling or regulating the amount of activating agent utilized in chloriding the composite. While molar excesses of the stoichiometric amount of activator needed to provide the catalyst with the chlorine content noted above is employed, we prefer to utilize up to about 30 percent molar excess and preferably up to about 20 percent molar excess of the stoichiometric amount necessary to react with the alumina support's surface hydroxyl groups. In a typical situation, the metal-alumina composite comprises from about 0.46 to about 0.49 weight percent noble metal, preferably platinum, on an eta or gamma alumina support and employing carbon tetrachloride as the activating agent of choice, we can utilize about 39 grams of carbon tetrachloride, preferably 19 grams of carbon tetrachloride, per 100 grams of platinum alumina composite. The molar excess of agent in the illustrations represent respectively about 30 percent and preferably about 16 percent excess agent needed to react with the alumina surface. We have found that treating the composite with an aluminum salt and controlling the amount of activation employed, the loss of noble metal from the composite can be essentially eliminated and the resulting catalyst possesses high isomerization activity.

The catalysts described herein and prepared according to the above procedure are employed to isomerized paraffins in the $C_4$ to $C_6$ range. Isomerization of the hydrocarbons enables the petroleum refiner to upgrade hydrocarbons to valuable gasoline components. Isomerization is of interest in that lead anti-knock compounds are gradually being eliminated from gasolines and isomerization of normal paraffins provides an increase in high octane blending components. For example, isomerization enables the refiner to increase the octane number of the fraction by converting the normal paraffins to isomers, such as normal butanes to isobutanes and normal hexanes to isoparaffins, such as 2,2-dimethylbutane. A blend of various isomeric paraffins provides a gasoline having a higher octane number than one consisting of normal paraffins. Generally, isomerization is conducted by introducing the isomerizable hydrocarbon together with hydrogen through a reaction zone containing the isomerization catalyst. Hydrogen to hydrocarbon mole ratios of from 0.05:1 to 5.0:1, preferably about 0.5:1 to 2:1 for pentanes and hexanes and 0.1:1 to 1:1 for butane are employed. The reaction conditions include temperatures generally in the range of about 200° to 400° F. with hydrocarbon streams chiefly of pentanes and hexanes being isomerized in the range of about 250° to 350° F. and butanes at about 300° to 400° F. Isomerization is normally effected under hydrogen pressure and may be carried out in a liquid or vapor phase. Suitably, pressures within the range of 300 to 700 p.s.i.g. are considered appropriate along with a liquid hourly space velocity, i.e., the volume of liquid charge per hour per volume of catalyst within the range of about 0.5 to 10.0.

In order to more fully illustrate the nature of our invention and the manner of practicing the same, the following examples are presented. In these examples the best mode contemplated by us for carrying out our invention is set forth.

EXAMPLES

The metal-alumina composite employed in the following examples was an unsulfided calcined platinum-alumina composite in the form of 1/16 inch extrudates composed of from about 0.46 to about 0.49 weight percent platinum on a predominantly eta-alumina support. In each example, a reactor having a bed length of 6 feet containing 1600 grams of composite was employed. The composites in the bed were respectively activated, in situ, as described below. In each instance, the composite, prior to contacting with the chloriding agent, was calcined at 900° F., 50 p.s.i.g. and with 270 pounds of air per hour per square foot until the moisture content of the composite reached 2 weight percent. This condition is achieved when the moisture content of the exit air from the reactor contains about 50 to 70 ppm water. In Examples 5 and 6, the composites were pretreated prior to calcination, with aluminum nitrate. Each reactor bed was equally divided into five catalyst sections with the aid of glass wool plugs and the analyses of the finished catalyst reported in the Table are based on a composite of the five catalyst sections. Each isomerization catalyst was evaluated by passing n-butane through the bed for 14 hours at conversion conditions of 335° F., 500 p.s.i.g., 8 LHSV and at a hydrogen to n-butane mole rate of 0.2:1.

In Examples 1 and 2, duplicate runs were conducted employing 2000 cc. (1600 grams) of a composite composed of 0.46 weight percent platinum on eta-alumina.

Each time the reactor was maintained at 525° F. and 270 pounds of air per hour per square foot of reactor cross-section was passed through the bed of composite together with 20 cc. (31.8 grams) of carbon tetrachloride per 100 cc. (80 grams) of composite for about ten hours. The resulting chlorided platinum-alumina catalysts were thereafter stabilized by heating for 2 hours at 1000° F. while passing nitrogen through the catalyst bed at the rate of 270 pounds per hour per square foot of reactor cross-section at 50 p.s.i.g. The temperature was subsequently decreased to 350° F. and the catalysts were further stabilized by treating for five hours with nitrogen containing 1.3 percent HCl at the rate of 270 pounds per hour per square foot of reactor cross-section at 50 p.s.i.g.

In Examples 3 and 4, the procedure of Examples 1 and 2 was repeated except the activation with carbon tetrachloride was conducted for about five hours.

In Example 5, the procedure used in Examples 1 and 2 was repeated except that the platinum-alumina composite was treated, prior to calcination at 900° F. and chloriding, with aluminum nitrate. The treatment involved impregnating the composite with an aqueous solution of aluminum nitrate, 830 grams of composite per batch being impregnated with 18.3 grams of aluminum nitrate [$Al(NO_3)_3 \cdot 9H_2O$] and 625 cc. of distilled water. After mixing thoroughly, the mix was allowed to stand for 1 hour and thereafter dried at 250° F. The dried material was thereafter calcined in the manner of the other examples. The chloriding procedure followed that set out in Examples 1 and 2.

In Example 6, the procedure of Example 5 was repeated except that activation with carbon tetrachloride was conducted for about 5 hours as in Examples 3 and 4. The catalysts of Examples 5 and 6 contained approximately 0.3 weight percent stabilizing alumina.

The following table summarizes the catalyst preparation procedures of Examples 1–6 and reports the results of the respective n-butane isomerizations conducted in the presence of each catalyst.

in terms of metal retention and high hydroisomerization activity.

We claim:

1. A process for the hydroisomerization of $C_4$ to $C_6$ n-paraffin which comprises contacting said paraffin under hydroisomerization conditions with a catalyst composed of a noble metal, an alumina support and chlorine, said catalyst prepared by treating a composite of a noble metal and alumina with an aluminum salt solution, calcining said treated composite in air at a temperature sufficient to decompose said aluminum salt to alumina wherein from about 0.1 to 2.0 weight percent alumina is introduced to said composite, and thereafter providing said treated composite with from 3.0 to 15.0 weight percent chlorine by contacting said composite with a conventional chloride activating agent.

2. A process according to claim 1 wherein said treating and calcining introduces from about 0.2 to 1.0 weight percent alumina to said catalyst.

3. A process according to claim 1 wherein said aluminum salt is aluminum nitrate, aluminum sulfate, aluminum chloride, aluminum bromide, aluminum iodide, aluminum chlorate, aluminum bromate, aluminum acetate or aluminum lactate.

4. A process according to claim 1 wherein said aluminum salt is aluminum nitrate.

5. A process according to claim 1 wherein said noble metal is platinum, where said aluminum salt is aluminum nitrate and where said activating agent is carbon tetrachloride.

6. A process according to claim 1 wherein said composite is chlorided by contacting with said chloride activating agent in an amount ranging from the stoichiometric amount to about 30 percent excess of the stoichiometric amount necessary to react with said alumina support's surface hydroxyl groups.

7. A process according to claim 6 wherein said activating agent is employed in an amount of from about 10 to 20 percent excess of said stoichiometric amount.

8. A process for the hydroisomerization of $C_4$ to $C_6$

TABLE

| | | Activation Procedure | | | Analysis of Catalyst | | | |
|---------|----------------|----------------------|----------------------|-----------------------------------------|------|-----------------|------|-----------------------------------|
| Example | Composite (cc) | % Pt in Composite    | $CCl_4$ Rate cc/hr   | $CCl_4$ Dosage; $CCl_4$, cc/100 cc Composite | % Pt | % Pt Retained   | % Cl | Wt % n-$C_4$ Converted to i-$C_4$ |
| 1       | 2000           | 0.46                 | 20                   | 20                                      | 0.276| 60.0            | 5.75 | 43.0                              |
| 2       | 2000           | 0.46                 | 20                   | 20                                      | 0.290| 63.0            | 5.55 | 33.0                              |
| 3       | 2000           | 0.46                 | 20                   | 10                                      | 0.432| 94.0            | 5.20 | 39.5                              |
| 4       | 2000           | 0.47                 | 20                   | 10                                      | 0.440| 93.6            | 4.90 | 38.5                              |
| 5       | 2000           | 0.49                 | 20                   | 20                                      | 0.402| 82.0            | 4.66 | 40.0                              |
| 6       | 2000           | 0.46                 | 20                   | 10                                      | 0.445| 96.7            | 4.7  | 41.0                              |

The data in the table, from a comparison of Examples 1 and 2 with Example 5, shows that pretreatment of the composite with aluminum nitrate prior to calcination and chloride activation had the effect of increasing platinum retention from about 60 to 82 percent. In Example 6, no discernible loss of platinum occurred when the pretreatment was employed. The pretreatment enabled varied amounts of chloriding agent to be employed while still providing the catalyst with high isomerization activity. It is apparent from the table that high conversion of normal paraffin to isomer occurred in the presence of the pretreated catalysts of Examples 5 and 6 albeit that these catalysts possessed the lowest chlorine contents. The pretreatment according to our invention enables the preparation of more reproducible catalysts n-paraffin which comprises contacting said paraffin under hydroisomerization conditions with a catalyst comprising an alumina support, about 0.01 to 2.0 weight percent of a noble metal on said support, about 0.1 to 2.0 weight percent alumina on said metal and support and about 3.0 to 15.0 weight percent chlorine, said alumina on said metal and support being effective for retaining said noble metal on the catalyst's surface during the addition of chlorine.

9. A process according to claim 8 wherein said catalyst comprises platinum on an eta alumina support, about 0.2 to 1.0 weight percent alumina on said platinum-support and about 4.0 to 8.0 weight percent chlorine.

* * * * *